United States Patent [19]

Primack et al.

[11] Patent Number: 5,087,784
[45] Date of Patent: Feb. 11, 1992

[54] AROMATIC ALKYLATION PROCESS AND APPARATUS

[75] Inventors: Harold S. Primack, Skokie; Ronald L. Cutshall, Mokena, both of Ill.

[73] Assignee: Amoco Corporation, Chicago, Ill.

[21] Appl. No.: 606,329

[22] Filed: Oct. 31, 1990

[51] Int. Cl.$^5$ .............................................. C07C 2/66
[52] U.S. Cl. ................................ 585/446; 585/467; 585/453; 203/DIG. 6; 502/527
[58] Field of Search ............... 585/467, 446, 453; 203/DIG. 6; 502/527

[56] References Cited

U.S. PATENT DOCUMENTS

| | | | |
|---|---|---|---|
| 3,713,615 | 1/1973 | Jones | 203/DIG. 6 |
| 4,720,336 | 1/1988 | Vora et al. | 208/46 |
| 4,751,057 | 6/1988 | Westerman | 422/197 |
| 4,837,396 | 6/1989 | Herbst et al. | 502/67 |
| 4,891,458 | 1/1990 | Innes et al. | 585/467 X |
| 4,973,780 | 11/1990 | Johnson et al. | 585/467 |

FOREIGN PATENT DOCUMENTS 0633595 11/1978 U.S.S.R. ................ 502/527

*Primary Examiner*—Asok Pal
*Assistant Examiner*—D. J. McGinty
*Attorney, Agent, or Firm*—Reginald K. Taylor; William H. Magidson; Ralph C. Medhurst

[57] ABSTRACT

An aromatic alkylation process comprising continuously feeding catalyst particles through at least one substantially vertically-positioned permeable tube disposed in a vessel surrounding said permeable tube, contacting said catalyst particles with at least one aromatic hydrocarbon and at least one alkylating agent under liquid phase alkylation conditions, continuously removing said catalyst particles from a lower end of said tube, and recovering said alkyl-substituted aromatic.

15 Claims, 1 Drawing Sheet

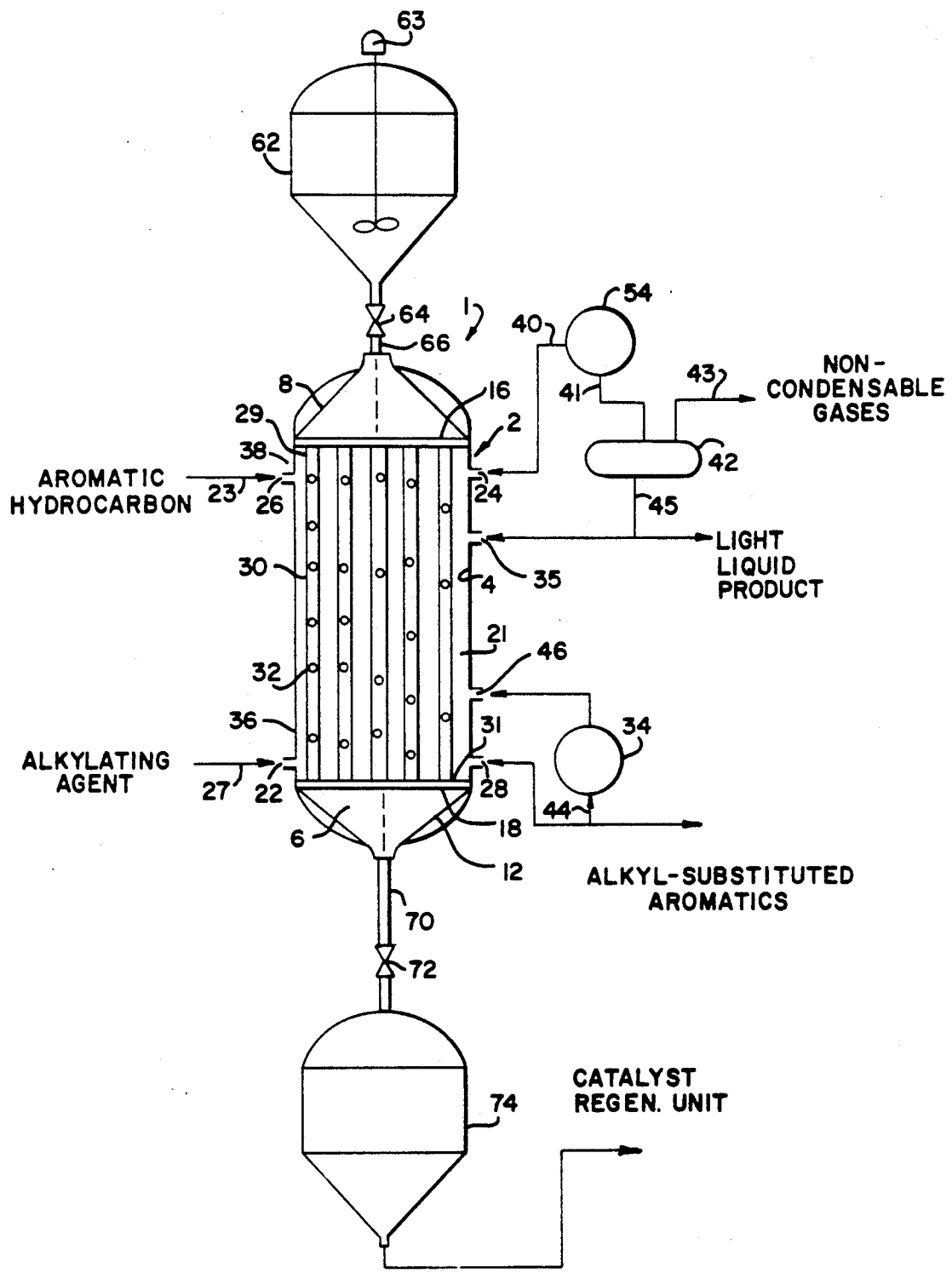

ic alkyla-
AROMATIC ALKYLATION PROCESS AND APPARATUS

FIELD OF THE INVENTION

The present invention relates to an aromatic alkylation process and apparatus for producing an alkyl-substituted aromatic by feeding catalyst particles through at least one substantially vertically-positioned permeable tube disposed in a vessel surrounding said permeable tube, contacting said catalyst particles with at least one aromatic hydrocarbon and at least one alkylating agent inside said permeable tube under liquid phase alkylation conditions, removing said catalyst particles from a lower end of said permeable tube, and recovering said alkyl-substituted aromatic.

BACKGROUND OF THE INVENTION

In an aromatic alkylation process, aromatic hydrocarbons, such as benzene and toluene, react with alkylating agents, such as ethylene and propylene, in the presence of a silica-containing molecular sieve catalyst to produce alkyl-substituted aromatics, such as ethylbenzene and ethyltoluene. Chemical intermediates resulting from aromatic alkylation processes include isopropylbenzene, which is used in the manufacture of phenol, and vinyl toluene monomers, which are used in the production of a variety of styrenic polymer materials. In regard to transportation fuels, the use of alkyl-substituted aromatics as blending agents for gasoline expand product volume and increase octane values. Further, aromatic alkylation processes provide a cost effective manner of reducing the amount of benzene in gasoline.

In the past, Friedel-Crafts type catalysts were used as the alkylation catalyst in aromatic alkylation processes. However, the use of these catalysts have numerous disadvantages, including corrosion problems, high regeneration costs, low yields of alkylates boiling in the gasoline range, and complicated separation processes of alkylated products.

These disadvantages can be avoided by employing processes that use crystalline zeolite catalysts which are non-corrosive, and from which the alkylation products can be more readily separated. Alkylation of aromatic hydrocarbons using a crystalline zeolite catalyst has heretofore been described in U.S. Pat. No. 2,904,607 which refers to alkylation of aromatic hydrocarbons with an olefin in the presence of a crystalline metallic aluminosilicate catalyst having uniform pore openings of 6-15 Angstroms.

While crystalline zeolite catalysts represent a distinct improvement over previously suggested Friedel-Crafts type catalyst, they have the disadvantage of producing unwanted quantities of impurities along with the desired alkyl aromatic product, thereby decreasing the overall Yield and selectivity for the product. Another problem with these types of catalysts is that they are subject to rapid deactivation, particularly under vapor phase reaction conditions where gaseous olefins can compete with aromatics for active catalyst sites and result in coking of the zeolite. Consequently, many prefer liquid phase alkylation conditions, for example, U.S. Pat. Nos. 3,641,177, 3,251,897, and 3,631,120.

U.S. Pat. No. 4,849,569 applies reactive-distillation to aromatic alkylation. Since in reactive-distillation the reaction is occurring concurrently with separation, the initial alkylation product is removed as soon as it is formed. Consequently, decomposition of the alkylation product and oligomerization of the olefins are minimized. Another advantage of the application of reactive-distillation to aromatic alkylation is increased energy efficiency due to the exothermic heat generated by the alkylation reaction being used to assist in separation.

Initial reactive-distillation processes did not have concurrent reaction and separation. In U.S. Pat. No. 3,579,309 there is disclosed a distillation column for carrying out organic chemical reactions using a catalyst, the column being formed with catalyst-receiving reaction vessels which are arranged outside the column between individual column tray outlet and inlet openings. Since the reaction and separation steps are not concurrent, this process is not considered energy efficient.

In U.S. Pat. Nos. 3,629,478, 3,634,534, and 3,634,535, there is disclosed a process that contacts reactants with a heterogeneous catalyst in the downcomers of the reactor. While this arrangement permits the reaction and separation to be performed in the same vessel, the practical design of downcomers to convey liquid through the catalyst with the limited liquid head available can result in very inefficient use of the space within the distillation reactor.

In U.S. Pat. No. 3,506,408, a multistage reaction apparatus is shown. The apparatus comprises a liquid feed inlet at the top of the apparatus, a gas inlet at the bottom of the apparatus, and a plurality of perforated trays containing catalyst beds positioned along the length of the reactor. The liquid passes downward through the catalyst on the trays and the gas zig-zags around the trays such that there is essentially no countercurrent contact of liquid and gas within the catalyst beds. As a result there can be very inefficient fractionation of vapor and liquid components.

All of the aromatic alkylation processes discussed hereinabove also have the additional disadvantage of having to take the reactor off line in order to replace deactivated catalyst. This can be a difficult and expensive process for fixed-bed catalyst systems, particularly the catalyst system disclosed in U.S. Pat. No. 4,849,569. In that system, particulate catalyst is contained in an array of closed cloth pockets supported by wire mesh. A typical column can have hundreds of these arrays that will need to be replaced individually by hand.

There is a need for an aromatic alkylation process that does not require shutting down the reactor to replace deactivated catalyst.

SUMMARY OF THE INVENTION

The present invention is a process for producing an alkyl-substituted aromatic comprising the steps of feeding catalyst particles downwardly by gravity through at least one substantially vertically-positioned permeable tube disposed in a vessel surrounding said permeable tube, contacting said catalyst particles with at least one aromatic hydrocarbon and at least one alkylating agent inside said permeable tube under liquid phase alkylation conditions, removing said catalyst particles from a lower end of said permeable tube, and recovering said alkyl-substituted aromatic. The objective of the present invention is to provide an alkylation process that does not require shutting down the reactor to replace deactivated catalyst. An essential feature of the process of the present invention is the flow of catalyst particles through the vessel in which the aromatic alkylation reaction occurs. This feature successfully addresses the aformentioned need by allowing for replacement of deactivated catalyst particles with fresh or regenerated catalyst without shutting down the aromatic alkylation process. In addition, by operating the aromatic alkylation process under liquid phase conditions, premature catalyst deactivation can be avoided.

In one embodiment, the present invention is a process for producing an alkyl-substituted aromatic comprising the steps of continuously feeding catalyst particles comprising a crystalline aluminosilicate zeolite in an alumina matrix downwardly by gravity through a plurality of substantially vertically-positioned permeable tubes disposed in a shell-like or shell distillation zone surrounding said permeable tubes, contacting said catalyst particles with at least one aromatic hydrocarbon selected from the group consisting of benzene, toluene, and xylene and at least one olefinic hydrocarbon inside said permeable tubes under liquid continuous phase alkylation conditions, continuously removing said catalyst particles from a lower end of said permeable tubes, and recovering said alkyl-substituted aromatic. The use of a plurality of permeable tubes allows for greater throughput. BY surrounding the permeable tubes with a shell-like distillation zone, the alkylation reaction occurring in said permeable tubes is forced to completion since the simultaneous fractionation and removal of the alkyl-substituted product away from the reaction zone does not allow the products to contribute to the reverse reaction. In addition, heat generated by the alkylation reaction can be used to aid in fractionation. Crystalline aluminosilicates zeolites are preferred because they have been found to have higher conversions in aromatic alkylation reactions in comparison to other silica-containing molecular sieves.

In another embodiment, the present invention is a process for producing an alkyl-substituted aromatic selected from the group consisting of ethyl- and propylbenzene, ethyl- and propyltoluene, ethylpropylbenzene, and ethylpropyltoluene, comprising the steps of continuously feeding catalyst particles consisting essentially of beta zeolite in an alumina matrix downwardly by gravity through a plurality of substantially vertically-positioned permeable tubes disposed in a shell-like distillation zone surrounding said permeable tubes, contacting said catalyst selected from the group consisting of benzene, toluene, and xylene and at least one gaseous olefinic hydrocarbon selected from the group consisting of ethylene and propylene inside said permeable tubes under alkylation conditions sufficient to provide a liquid continuous phase and to permit radial flow of said aromatic and olefin into at least one opening in said permeable tubes and radial flow of said alkyl-substituted aromatic out of said opening, continuously removing said catalyst particles from a lower end of said permeable tubes, and recovering said alkyl-substituted aromatic. Beta zeolite catalyst are preferred because they have been found to have lower deactivation rates in aromatic alkylation reactions in comparison to other crystalline aluminosilicates zeolites.

In another aspect, the present invention is a catalytic conversion reactor comprising a normally substantially vertically extending vessel having a central longitudinally extending axis and an inner wall, at least one permeable tube arranged in said vessel substantially parallel to said axis, said permeable tube having an upper end fixed to an upper tube plate and in fluid communication with a catalyst inlet chamber above said upper tube plate, said permeable tube further having a lower end fixed to a lower tube plate and in fluid communication with a catalyst outlet chamber below said lower tube plate, a shell-like distillation zone defined by said upper tube plate, lower tube plate and inner wall, a condenser above said catalyst inlet chamber, and a reboiler below said catalyst outlet chamber.

BRIEF DESCRIPTION OF THE DRAWING

The drawing represents a side view of a reactor system in accordance with the present invention.

DETAILED DESCRIPTION OF THE INVENTION

The present invention is an aromatic alkylation process wherein an aromatic hydrocarbon is contacted with an alkylating agent in a reactor under liquid phase alkylation conditions in the presence of a particulate alkylation catalyst that is moving downward by gravity through at least one permeable tube disposed in said reactor.

Suitable aromatic hydrocarbons include benzene, toluene, ortho-xylene, meta-xylene, para-xylene, ethylbenzene, ortho-ethyltoluene, meta-ethyltoluene, para-ethyltoluene 1,2,3-trimethylbenzene or mesitylene, normal propylbenzene and isopropylbenzene. Higher molecular weight alkylaromatic hydrocarbons produced by alkylation of aromatic hydrocarbons with olefin polymers are also suitable for use in the present invention. Examples of such products are hexylbenzene, nonylbenzene, dodecyltoluene, and pentadecyltoluene. Other aromatic hydrocarbons suitable for use in the present invention include those having two or more aryl groups, such as diphenyl, diphenylmethane, triphenyl, and triphenylmethane. Examples of other aromatic hydrocarbons within the scope of this invention include materials containing condensed benzene rings, such as naphthalene, alpha-methylnaphthalene, betamethylnaphthalene, anthracene, phenanthrene, and naphthacene. Of the above aromatic hydrocarbons, benzene, toluene, and xylene are preferred.

A suitable source for aromatic hydrocarbons is a refinery total reformate stream. In general, such a stream has in mol percent about 19.5-35% paraffins, 0.5-2%napthenes, and 60-80% aromatics. More specifically, a typical composition of such a stream in mol percent is about 0.5% $C_4$ paraffins, 8.9% $C_5$ paraffins, 13.2% $C_6$ paraffins, 5.5% $C_7$ paraffins, 0.8% $C_8$ paraffins, 0.1% $C_9$ paraffins, 0.3% $C_5$ napthenes, 0.3% $C_6$ napthenes, 0.2% $C_7$ napthenes, 0.1% $C_8$ napthenes, 8.4% $C_6$ aromatics, 20.4% $C_7$ aromatics, 19.8% $C_8$ aromatics, 13.2% $C_9$ aromatics, 6.5% $C_{10}$ aromatics, and 1.8% $C_{11}+$ aromatics. Preferably, the aromatic hydrocarbon source is a light fraction of the total reformate stream. In general, such a stream has in mol percent about 40-59% paraffins, 1-3% napthenes, and 40-59% aromatics. More specifically, a typical composition of such a stream in mol percent is about 1.6% $C_4$ paraffins, 12.2% $C_5$ paraffins, 20.6% $C_6$ paraffins, 12.8% $C_7$ paraffins, 5.5% $C_8$ paraffins, 0.5% $C_9$ paraffins, 0.6% $C_5$ napthenes, 0.7% $C_6$ napthenes, 0.7% $C_7$ napthenes, 0.4% $C_8$ napthenes, nil $C_9$ napthenes, 11.1% $C_6$ aromatics, 28.7% $C_7$ aromatics, and 4.6% $C_8$ aromatics.

Suitable alkylating agents include alcohols, formaldehyde, ethers, and any other acyclic compounds having at least one reactive alkyl radical. Suitable alcohols are methanol, ethanol, n-propanol, and isopropanol. The olefins can be $C_2$ to $C_{20}$ olefins, preferably $C_2$-$C_{12}$ olefins, including normal and branched forms thereof. For example, suitable olefins are ethylene, propylene, butylene, isobutylene, 1-pentene, 2-pentene, 1-hexene, 2-hexene, 2,3-dimethyl-1-pentene, 1-octene, diisobutylene, 1-nonene and 1-decene, dodecene and the like. In a preferred embodiment, the olefins are $C_2$-$C_6$, most preferably ethylene and propylene.

The present invention can be practiced with alkylating agents wherein the ethylene and propylene olefinic hydrocarbons are present in gas streams. The gas streams are present in petroleum refineries from various refinery installations, including thermal cracking units, catalytic cracking units, thermal reforming units, coking units, and polymerization units. A typical analysis, in molpercent consists of about 3.9% nitrogen, 0.2% carbon monoxide, 5.4% hydrogen, 37.8% methane, 10.3% ethylene, 24.7% ethane, 6.5% propylene, 10.7% propane, and 0.5% $C_4$ hydrocarbons. carbons.

A suitable aromatic hydrocarbon to alkylating agent feed ratio is about 1:1 to 25:1, preferably about 1:1 to 4:1.

Catalysts suitable for use in the present invention can be any silica-containing molecular sieve, including but not limited to aluminosilicates, borosilicates, gallosilicates, and chromosilicates.

In a preferred embodiment the catalyst is a crystalline aluminosilicate zeolite having a structural formula of:

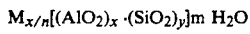

$$M_{x/n}[(AlO_2)_x \cdot (SiO_2)_y]m\ H_2O$$

where M is a cation of valence n, m is the number of water molecules, and the sum of x and y is the total number of tetrahedra in the unit cell. The ratio of y/x can vary depending on the structure. Either naturally-occurring or synthetic aluminosilicates may be used. Among the naturally-occurring aluminosilicates which can be employed are faugasite, clinoptolite, mordenite and dachiardite. These aluminosilicates have been found to have the ability to absorb benzene and larger aromatic hydrocarbons. Crystalline aluminosilicate zeolites suitable for use as the catalyst of the present invention can be Y zeolite, X zeolite, beta zeolite, L zeolite, omega zeolite, and modifications of such zeolites.

In addition to silica-containing molecular sieves, the catalyst of the present invention further comprises a porous, refractory inorganic binder which is combined, dispersed or otherwise intimately admixed with the zeolite in order to have the physical strength and attrition resistance for industrial use. Suitable inorganic binders include alumina, silica, clays, bauxite, zirconium oxide, hafnium oxide, titanium oxide, zinc oxide, and magnesia.

Suitable methods for composition the zeolite material with the binder can be found in U.S. Pat. Nos. 4,808,763 and 4,738,768 which are herein incorporated by reference.

The catalyst particle size can range from about ¼-1/100 of an inch. In a preferred embodiment, the catalyst particle size can be not more than about 1/32 of an inch, preferably not more than about 1/64 of an inch, most preferably not more than about 1/100 of an inch. Also in a preferred embodiment, the catalyst comprises beta zeolite in an alumina support and has a pore volume of about 0.25–0.50 cc/q, preferably about 0.25–0.35 cc/g, most preferably about 0.30–0.35 cc/g in pores having a diameter greater than about 450 Angstroms.

In somewhat greater detail, this invention involves an aromatic alkylation process comprising the steps of feeding catalyst particles downwardly by gravity through at least one substantially vertically-positioned permeable tube 30 disposed in a vessel 2 surrounding said tube 30, contacting said catalyst particles with an aromatic hydrocarbon and at least one alkylating agent inside said permeable tube under liquid phase alkylation conditions, removing said catalyst particles from a lower end of said permeable tube 30, and recovering an alkyl-substituted aromatic.

An essential feature of a process of the present invention is the flow of catalyst particles through a reactor 1. The movement of catalyst particles through the reactor 1 can be continuous or intermittent, preferably continuous. Further, the movement of catalyst can occur as a dense bed of catalyst particles moving by gravity in plug flow or as a fluidized-bed. The rate of movement of the catalyst particles through the reactor 1 depends on the relative rate and severity of operation. The rate can be constant or varied. In a preferred embodiment, the catalyst particles are spherically-shaped to facilitate movement through the reactor 1.

The flow of catalyst particles through the reactor 1 originates at the catalyst feed drum 62 positioned above the reactor 1. Inside the catalyst feed drum 62 is a mixer 63 to assist in making up a fresh catalyst slurry. The catalyst feed drum 62 can be filled with catalyst slurry by filling partially with a suitable liquid, then adding dry catalyst particles. In one embodiment, the liquid can be mixed in a separate mix tank (not shown) and then pumped to the catalyst feed drum 62. An example of a suitable catalyst liquid can be a liquid aromatic hydrocarbon. Fresh catalyst particles from the catalyst feed drum 62 flow through a catalyst inlet valve 64 into a catalyst inlet transfer line 66 down to the reactor 1. Liquid can be injected into the catalyst inlet transfer line 66 to further fluidize the catalyst and facilitate the movement of catalyst.

After passing through the permeable tubes 30, the catalyst particles flow downwardly by gravity to a catalyst withdrawal drum 74. A catalyst outlet valve 72 located in the catalyst outlet transfer line 70 controls the flow of catalyst from the reactor 1 to the catalyst withdrawal drum 74. The catalyst particles exiting the catalyst withdrawal drum 74 can be recycled directly back to the catalyst feed drum 62 or sent to a regeneration unit prior to recycle. Whether the catalyst particles are sent to a regeneration unit prior to recycling to the feed drum 62 depends upon the degree to which the catalyst particles are spent. This can depend upon the type of catalyst and the residence time of the catalyst in the tube 30. One way of determining whether the catalyst is spent is to monitor percent conversion of reactants to products with time to observe any decrease.

A suitable catalytic conversion reactor 1 for the process of the present invention comprises a normally substantially vertically extending vessel 2 having a central longitudinally extending axis 6, and at least one permeable tube 30 arranged in said vessel 2 substantially parallel to said axis 6, said permeable tube 30 having an upper end 29 fixed to an upper tube plate 16 and in fluid communication with a catalyst inlet chamber 8 above said upper tube plate 16, said permeable tube 30 further having a lower end 31 fixed to a lower tube plate 18 and in fluid communication with a catalyst chamber 12 below the lower tube plate 18. The reactor 1 further comprises a condenser 54 positioned above said catalyst inlet chamber 8, and a reboiler 34 positioned below said catalyst outlet chamber 12.

The vessel 2 has an inner wall 4, a first inlet port 22 defined in a lower end 36 of said vessel 2, a first outlet port 28 defined in said lower end 36 of said vessel opposite said first inlet port 22, a second outlet port 24 defined in an upper end 38 of said vessel 2, and a second inlet port 26 defined in said upper end 38 of said vessel 2 opposite said second outlet port 24. The vessel 2 also has a shell-like distillation zone 21 which is defined by said upper tube plate 16, lower tube plate 18, and inner wall 4. The distillation zone 21 can contain baffles (not shown) to increase gas residence time, mixing, and heat and mass transfer. The distillation zone 21 can also contain any conventional distillation packing, preferably Berl saddles.

Extending through said distillation zone 21 substantially parallel to said axis 6 is at least one permeable tube 30. The tube 30 functions as a conduit for the movement of catalyst particles downward by gravity through the reactor 1. The dimensions of the tube 30 can vary depending on the process conditions. Preferably, the tube 30 has a diameter of 0.5–3 inches and a length of 8–96 feet. The tube can be arranged in the shape of a cylinder, square, triangle, or diamond, preferably a cylinder. Preferably, there is a plurality of tubes 30. The exact number of tubes 30 can vary depending on the process conditions. The tube 30 can be fabricated from metal, ceramic, polymer, wire, or screen and can be rolled or extruded. Permeability in the tube is established by at least one opening 32, preferably a plurality of openings 32. The opening 32 can be established by drilling, punching, or cutting the tube 30. The size of the opening 32 must be large enough to permit the flow of reactants into vent the flow of catalyst particles out of the tube into the distillation zone 21 of vessel 2. Thus, the catalytic convergion reaction takes place solely on the inside of the tube 30, and not in the shell-like distillation zone 21.

Reactants enter the reactor 1 through inlet ports 22 and 26 and flow into the shell-like distillation zone 21. From the distillation zone 21, the reactants flow radially inward through the opening 32 of the tube 30, thereby contacting the catalyst as the catalyst particles flow downward by gravity from the catalyst feed drum 62 through the tubes 30 into the catalyst withdrawal drum 74. Products of the reaction flow radially outward through the opening 32 of the tube 30 into the distillation zone 21 where they are separated from the reactants by fractionation. Gaseous products and unreacted light reactants exit the vessel 2 at the outlet port 24 into a condenser 54. An effluent stream 41 exiting from the bottom of the condenser 54 is fed to a separator drum 42 where noncondensible gases exit the top of the separator drum 42 in stream 43. A light liquid product stream 45 exits the bottom of the separator drum 42. In one embodiment, a portion of the light liquid product 45 is refluxed to port 35. In another embodiment, substantially all of the liquid stream 45 is refluxed to the of vessel 2 at port 35. In another embodiment, the light liquid product stream 45 is fed to a separate fractionation tower (not shown), with the bottoms from said tower being refluxed to the vessel 2 at port 35. A bottoms stream 44 exits the vessel 2 at the outlet port 28. A portion of the bottoms stream 44 is fed to the reboiler 34 and recycled to the vessel 2 at port 46. The heat from the reboiler 34 is used to separate products from reactants in distillation zone 21. In one embodiment, the bottoms stream is fed to a fractionation tower (not shown), with the overhead of the tower being recycled to the vessel 2 at port 46.

An essential feature of the present invention is liquid phase alkylation conditions. This can be accomplished by maintaining a liquid level in the distillation zone 21 sufficient to keep the catalyst substantially immersed during the alkylation reaction. In a preferred embodiment, the alkylation reaction occurs in a liquid continuous phase which is defined as a liquid phase having a continuous flow of vapor bubbling up therethrough. The origin of the vapor can be, for example, a gaseous alkylating agent or a hot reboiler stream recycled to the vessel 2.

In the process of the present invention, it is preferred that the process conditions in the reactor 1 be such that reactants are permitted to flow radially inward from the distillation zone 21 through the opening 32 of the tube 30, and products are permitted to flow radially outward from the inside of tube 30 through the opening 32 into the distillation zone 21. Such conditions can include a temperature of about 250–750 deg F, preferably about 300–450 deg F, a pressure of about 1–100 atms, preferably about 1–30 atms, and an alkylating aqent weight hourly space velocity of about 0.1–20 $hr^{-1}$.

In a preferred process, the process of the present invention can be run as follows. A gaseous hydrocarbon-containing olefin stream 27 comprising ethylene and propylene is fed into the reactor 1 at inlet port 22 located at the lower end 36 of vessel 2. A liquid hydrocarbon-containing aromatic stream 23 comprising benzene, toluene, and xylene is fed into the reactor 1 at inlet port 26 located at the upper end 38 of vessel 2. The ratio of aromatic to olefin in the reactor 1 is about 4:1 to 15:1. Operating conditions present in the reactor 1 include a temperature of about 300–450 deg F, a pressure of about 1–30 atm, and a weight hourly space velocity of about 0.1–20 $hr^{-1}$. The aromatic and olefinic hydrocarbons flow into the distillation zone 21 of the vessel 2 which is filled with a liquid-containing aromatic. From the distillation zone 21, the aromatic and olefinic hydrocarbons flow radially through the openings 32 into the tubes 30. Once inside the tubes 30, the aromatic and olefinic hydrocarbons react in the presence of continuously moving catalyst particles comprising beta zeolite in an alumina matrix to form alkyl-substituted aromatic comprising ethyl- and propylbenzene, ethyl- and propyltoluene, ethylpropyltoluene, and ethylpropylbenzene. These alkyl-substituted aromatics flow radially out of the tubes 30 into the distillation zone 21 of the vessel 2 where there are immediately separated from unreacted aromatics and olefinic hydrocarbons by distillation. To assist in distillation, the distillation zone 21 is filled with Berl saddles. An overhead stream 40 comprising unreacted ethylene, propylene, benzene, toluene, and xylene exits the reactor at port 24. This overhead stream 40 is fed to an overhead condenser 54. The effluent from the condenser 54 is fed to a separator drum 42. Noncondensable gases, such as unreacted ethylene and propylene, exit the top of the separator drum 42 in stream 43. Light liquid products, including benzene, toluene, and xylene, exit the bottom of the separator drum 42 in stream 45. A substantial portion of the light liquid product stream 45 is refluxed to the upper end 38 of the vessel 2. The remainder of the light liquid product 45 is recovered as product. A bottoms stream 44 comprising ethyl- and propylbenzene, ethyl- and propyltoluene, ethylpropyltoluene, and ethylpropylbenzene exits the distillation 21 at the bottoms port 28. A portion of the bottoms stream 44 is fed to a reboiler 34 and recycled back to the lower end 36 of the vessel 2.

We claim:

1. A process for producing an alkyl-substituted aromatic comprising the steps of feeding catalyst particles downwardly by gravity through at least one substantially vertically-positioned permeable tube disposed in a shell distillation zone surrounding said permeable tube, contacting said catalyst particles with at least one liquid aromatic hydrocarbon and at least one gaseous alkylating agent inside said permeable tube under liquid continuous phase alkylation conditions to produce said alkyl-substituted aromatic, removing said catalyst particles from a lower end of said permeable tube, separating said alkyl-substituted aromatic from said alkylating agent by fractionation within said shell distillation zone, and recovering said alkyl-substituted aromatic from a lower end of said shell distillation zone.

2. A process of claim 1 wherein said alkyl-substituted aromatic comprises at least one member selected from the group consisting of ethyl- and propylbenzene, ethyl and propyltoluene, ethylpropylbenzene, and ethylpropyltoluene.

3. A process of claim 1 wherein said aromatic hydrocarbon comprises at least one member selected from the group consisting of benzene, toluene, and xylene.

4. A process of claim 1 wherein said alkylating agent comprises an olefinic hydrocarbon.

5. A process of claim 4 wherein said olefinic hydrocarbon comprises at least one member selected from the group consisting of ethylene and propylene.

6. A process of claim 1 wherein the catalyst particles comprise a silica-containing molecular sieve in a refractory inorganic oxide matrix.

7. A process of claim 6 wherein said molecular sieve comprises a crystalline aluminosilicate zeolite.

8. A process of claim 7 wherein said zeolite consists essentially of beta zeolite.

9. A process of claim 6 wherein the said matrix consists essentially of alumina.

10. A process for producing an alkyl-substituted aromatic comprising the steps of:

(a) continuously feeding catalyst particles comprising a crystalline aluminosilicate zeolite in an alumina matrix downwardly by gravity through a plurality of substantially vertically-positioned permeable tubes disposed in a shell distillation zone surrounding said permeable tubes;

(b) contacting said catalyst particles with at least one liquid aromatic hydrocarbon selected from the group consisting of benzene, toluene, and xylene and at least one gaseous olefinic hydrocarbon inside said permeable tubes under liquid continuous phase alkylation conditions to produce said alkyl-substituted aromatic;

(c) continuously removing said catalyst particles from a lower end of said permeable tubes;

(d) separating said alkyl-substituted aromatic from said olefinic hydrocarbon by fractionation within said shell-like distillation zone; and (e) recovering said alkyl-substituted aromatic from a lower end of said shell distillation zone.

11. A process of claim 10 wherein said alkyl-substituted aromatic is selected from the group consisting of ethyl- and propylbenzene, ethyl-and propyltoluene, ethylpropylbenzene, and ethylpropyltoluene.

12. A process of claim 10 wherein said olefinic hydrocarbon is selected from the group consisting of ethylene and propylene.

13. A process of claim 10 wherein said zeolite comprises beta zeolite.

14. A process of claim 13 wherein said zeolite consists essentially of beta zeolite.

15. A process for producing an alkyl-substituted aromatic selected from the group consisting of ethyl- and propylbenzene, ethyl- and propyltoluene, comprising the steps of:

(a) continuously feeding catalyst particles consisting essentially beta zeolite in an alumina matrix downwardly by gravity through a plurality of substantially vertically-positioned permeable tubes disposed in a shell distillation zone surrounding said permeable tubes;

(b) contacting said catalyst particles with at least one liquid aromatic hydrocarbon selected from the group consisting of benzene, toluene, and xylene and at least one olefinic hydrocarbon selected from the group consisting of ethylene and propylene inside said permeable tubes under alkylation conditions sufficient to provide a liquid continuous phase and to permit radial flow of said aromatic and said olefin into at least one opening located in said tubes and to permit radial flow of said alkyl-substituted aromatic out of said opening;

(c) continuously removing said catalyst particles from a lower end of said permeable tubes;

(d) separating said alkyl-substituted aromatic from said olefinic hydrocarbon by fractionation within said shell distillation zone; and (e) recovering said alkyl-substituted aromatic from a lower end of said shell distillation zone.

* * * * *